(12) United States Patent
Kopperl et al.

(10) Patent No.: US 6,586,756 B1
(45) Date of Patent: Jul. 1, 2003

(54) APPARATUS INCLUDING SULFUR BULB FOR ACCELERATING FADING OF LIGHT SENSITIVE MATERIALS

(75) Inventors: David F. Kopperl, Rochester, NY (US); Howard C. Brayman, Pittsford, NY (US)

(73) Assignee: Eastman Kodak Company, Rochester, NY (US)

( * ) Notice: Subject to any disclaimer, the term of this patent is extended or adjusted under 35 U.S.C. 154(b) by 456 days.

(21) Appl. No.: 09/609,660

(22) Filed: Jun. 30, 2000

(51) Int. Cl.[7] .................. G21G 4/00; G01N 17/00; H01J 17/20
(52) U.S. Cl. ................ 250/493.1; 73/865.6; 313/572
(58) Field of Search ................. 250/492.1, 493.1, 250/458.1, 504; 73/865.6; 315/248, 344; 362/263; 436/172; 313/567, 637, 643

(56) References Cited

U.S. PATENT DOCUMENTS

| | | | |
|---|---|---|---|
| 4,760,748 A | * | 8/1988 | Katayanagi et al. ....... 73/865.6 |
| 4,817,447 A | * | 4/1989 | Kashima et al. ........... 73/865.6 |
| 5,136,886 A | * | 8/1992 | Neigoff et al. ............. 73/865.6 |
| 5,138,892 A | * | 8/1992 | Suga ......................... 73/865.6 |
| 5,206,518 A | | 4/1993 | Fedor et al. |
| 5,404,076 A | * | 4/1995 | Dolan et al. ................ 313/572 |
| 5,734,115 A | | 3/1998 | Camp et al. |
| 5,767,423 A | | 6/1998 | Camp et al. |

* cited by examiner

Primary Examiner—John R. Lee
Assistant Examiner—James P. Hughes
(74) Attorney, Agent, or Firm—Raymond L. Owens

(57) ABSTRACT

An apparatus for subjecting light sensitive materials to visible radiation is disclosed which minimizes the amount of heat generated. The apparatus includes a source of visible radiation including at least one microwave energy responsive sulfur bulb and applies microwave energy to the sulfur bulb to cause the sulfur bulb to emit visible light. The apparatus further includes a holder defining a surface for receiving light sensitive materials located relative to the microwave energy responsive sulfur bulb. A light diffusing assembly is disposed relative to the sulfur bulb and responsive to the visible light emitted by the sulfur bulb to illuminate light sensitive materials received by the holder with diffused uniform visible light.

2 Claims, 4 Drawing Sheets

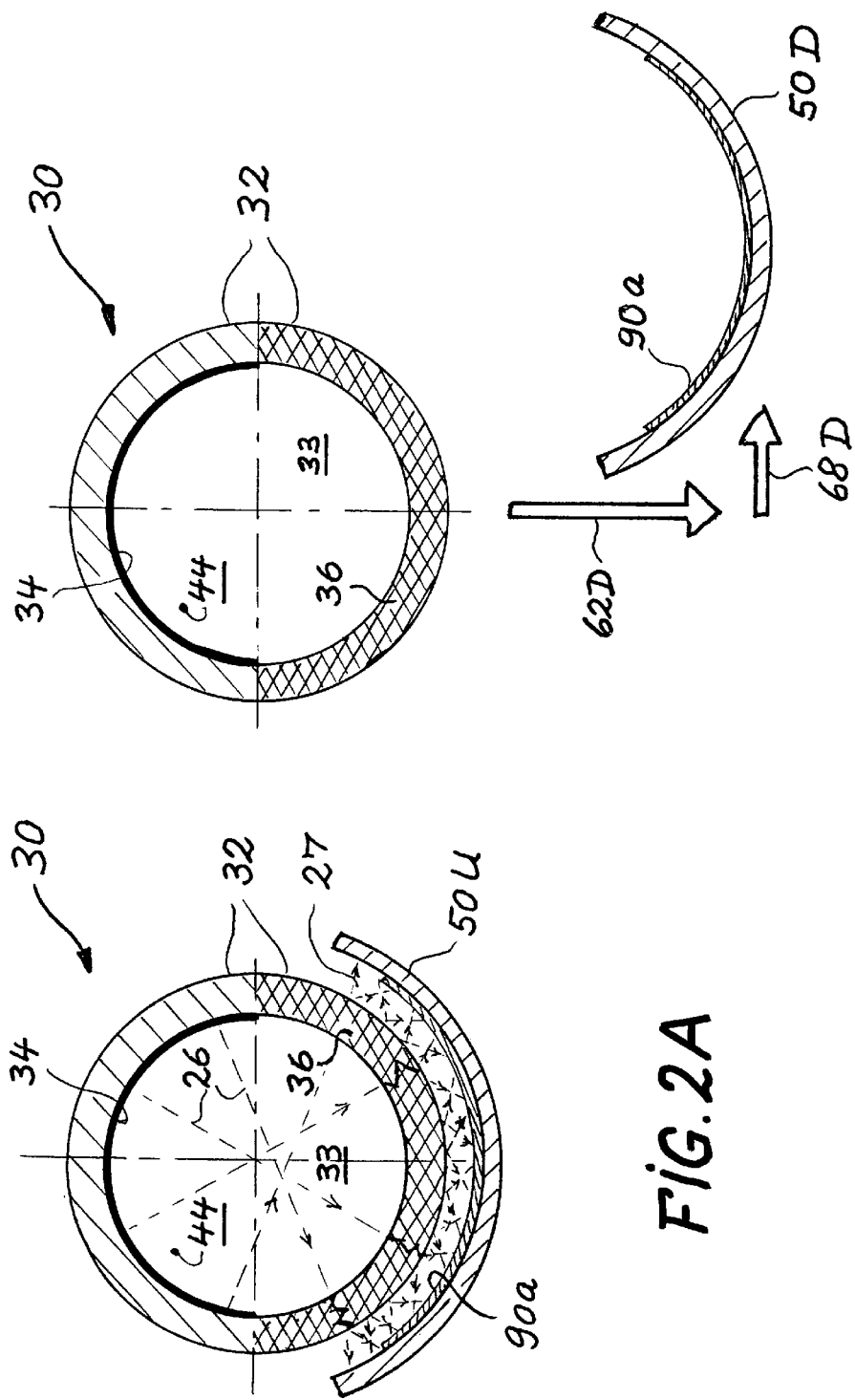

APPARATUS INCLUDING SULFUR BULB FOR ACCELERATING FADING OF LIGHT SENSITIVE MATERIALS

FIELD OF THE INVENTION

The present invention relates to producing accelerated aging in light sensitive materials.

BACKGROUND OF THE INVENTION

Weathering units and fade units are used to generate accelerated aging or fading of light sensitive materials by exposing the light sensitive materials to incident radiation levels above the levels typically found in office or home environments.

Existing units rely on high intensity xenon discharge lamps to create levels of incident radiation that are 2 to 4 times as intense as the radiation from the sun. These systems typically employ lamps that require 6000–12000 watts of electrical power to operate.

Much of the energy given off by such lamps is in the form of heat. To accommodate the heat generated by these lamps, accelerated aging units require large amounts of cooling air to keep the light sensitive materials at ambient temperature. Alternatively, such units only operate above ambient temperatures.

Accelerated fade units also require complex mechanical systems to ensure all the light sensitive materials are subject to the same, total amount of incident radiation no matter where they are located on a sample plane.

Such systems cause difficulty in testing the accelerated aging of light sensitive materials where the predominant source of aging will be due to incident light radiation, as the results are confounded by the use of elevated temperatures during the aging tests.

Alternatively, these systems can operate at reduced light levels to maintain the ambient temperature conditions. This removes the difficulty of interpreting the accelerated aging data, but it requires a longer period of time to perform the test procedures due to the use of lower light levels.

U.S. Pat. No. 4,760,748, issued to Kataynagi, et al, on Aug. 2, 1988, discloses an accelerated fade system based on a central light source, whereby a sample plane carrying light sensitive material rotates around a central light source. Thermal deterioration of the light sensitive material is inhibited by a cold air guide which encloses a portion of the rotating sample plane. The Kataynagi et al structure permits a large amount of light sensitive material to be loaded on the sample plane at one time, but requires a rotating sample assembly and an auxiliary cooling system.

U.S. Pat. No. 5,206,518, issued to Fedor, et al., on Apr. 27, 1993, discloses an accelerated fade unit based on a bank of lamps having an appropriate barrier array with a multiple detector feedback system to achieve a uniform power distribution over the sample plane. The Fedor et al structure permits a large amount of sample material to be loaded on the sample plane at one time, and it does not require any movement of the sample plane to maintain uniformity of light exposure at the sample plane. Fedor et al suffer from certain limitations. They require multiple lamps to obtain spatial uniformity of the incident light. They also require a complex system of detectors and feedback circuitry to control the lamp outputs individually. Finally, they use cooling air at the sample plane for temperature control.

Commonly assigned U.S. Pat. No 5,734,115, issued to Camp, et. al. on Jun. 16, 1998, employ an integrating sphere to allow the light sensitive material to remain stationary during the test. Camp et. al. suffer from certain design limitations in that the amount of light sensitive material that can be accommodated by the accelerated fade unit is limited to approximately 20 square inches of material at one time.

Commonly-assigned U.S. Pat. No. 5,767,423, issued to Camp, et. al., on Dec. 4, 1996 discloses a cooled sample holder for use in an accelerated fade apparatus that eliminates the need for external air cooling. Camp et. al. suffers from certain limitations. The disclosed holders are only capable of handling several square inches of light sensitive materials at any one time.

SUMMARY OF THE INVENTION

It is an object of the present invention to provide improved apparatus for the accelerated aging of light sensitive materials at high levels of incident radiation without suffering substantial heat problems.

It is a further object of the present invention to create high levels of incident radiation at only slightly elevated ambient temperatures.

It is another object of the present invention to operate at slightly elevated temperature without requiring additional cooling capabilities.

It is yet a further object of the present invention to permit for a large sample plane without requiring any complex mechanical subsystems.

A still further object of the present invention is to provide a uniform and stable source of incident radiation.

It is a further object of the present invention to provide for easy addition and removal of light sensitive materials from the apparatus.

These objects are achieved in an apparatus for subjecting light sensitive materials to visible radiation while minimizing the amount of heat generated, comprising:

(a) a source of visible radiation including at least one microwave energy responsive sulfur bulb;

(b) means for applying microwave energy to the microwave energy responsive sulfur bulb to cause such microwave energy responsive sulfur bulb to emit visible light;

(c) a holder defining a surface for receiving light sensitive materials located relative to the microwave energy responsive sulfur bulb; and (d) a light diffusing assembly disposed relative to the microwave energy responsive sulfur bulb and responsive to the visible light emitted by the microwave energy responsive sulfur bulb to illuminate light sensitive materials received by the holder with diffused uniform visible light.

A microwave energy responsive sulfur bulb provides a stable visible light source which does not produce excessive quantities of heat.

It is a feature of the present invention that microwave energy responsive sulfur bulbs are commercially available.

BRIEF DESCRIPTION OF THE DRAWINGS

FIG. 2A is a schematic section view of the apparatus of FIG. 1, taken along the section line 2—2, and showing the sample holder in an operative up position;

FIG. 2B is a section view of the apparatus of FIG. 1 taken along the section line 2—2 and showing the sample holder in a down-position and laterally translated to provide for loading/unloading of samples to be tested;

DETAILED DESCRIPTION OF THE PREFERRED EMBODIMENTS

Figure 1:
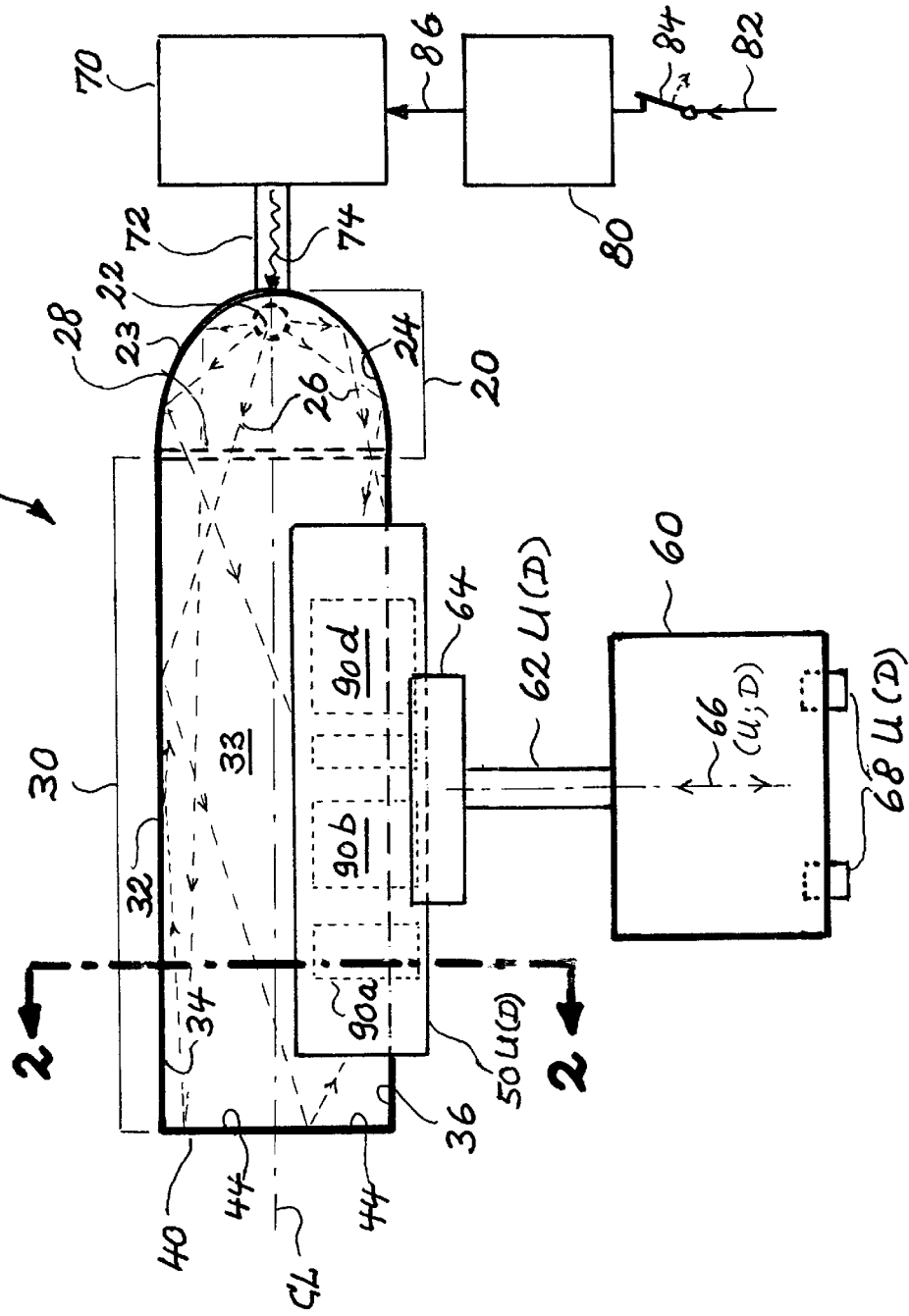
FIG. 1 is a schematic side view of a fading apparatus in accordance with the present invention.

Turning first to FIG. 1, there is shown a fading apparatus 10 for subjecting light sensitive materials to visible radiation while minimizing the amount of heat generated. As shown, there is provided a light diffusing assembly 30 disposed relative to a microwave energy responsive sulfur bulb light source 20 having a sulfur bulb 22. The microwave energy responsive sulfur bulb light source 20 can be of a construction well known in the art. In operation, a microwave generator 70 under the control of a power supply 80 causes the production of microwave energy which illuminates the microwave energy responsive sulfur bulb 22 via a waveguide 72 to provide guided microwaves 74 to be directed at the bulb 22. In turn, the microwave energy responsive sulfur bulb 22 produces visible light 26 which will illuminate light sensitive materials to cause their aging or fading. The light diffusing assembly 30 includes a light pipe 32 defining a cavity 33 for receiving light. This light is projected by an arcuate reflective portion 34. The arcuate reflective portion 34 is fastened to the internal surface of the light pipe 32 in the cavity 33. Also, a planar reflector 44 is fastened to an inside of an end surface 40 of the light pipe 32 in the cavity 33. A parabolic reflector 24 is disposed relative to the microwave energy responsive sulfur bulb 22 along a parabolic surface 23 of the light source 20. In operation, visible light produced by the microwave energy responsive sulfur bulb 22 is reflected off the parabolic reflector 24 into the cavity 33 via a transparent window 28.

An arcuate diffusive portion 36 diffuses the light received from within the cavity 33 and directs diffused light 27 from the cavity 33 towards a sample holder 50 which is disposed outside the cavity 33 proximate the diffusive portion 36. The diffusive portion 36 can be fastened to an internal surface of the light pipe 32 for transmitting diffused light through a light-transmissive wall of the light diffusing assembly 30. Alternatively, as shown schematically in FIG. 2A, the diffusive portion 36 can extend through the wall of the cavity 33 to provide uniformly diffuse exposure of light sensitive samples positioned on the sample holder 50.

The sample holder 50 is formed with a surface for receiving light sensitive samples (Samples 90a–90d in FIG. 1, and Samples 90a–90j in FIG. 4), and this surface is arcuately disposed in relation to the outside surface of the light pipe 32 in a position where diffuse light will pass from the light pipe 32 onto the light sensitive samples to be tested.

The sample holder 50 is supported by a mounting bracket 64 to which a piston rod 62 is attached. The piston rod 62 extends into a motion actuator 60 for vertical motion actuation 66 to provide an up position 50U of the sample holder 50 for exposing samples in the fading apparatus 10, as depicted in FIG. 1. The motion actuator 60 includes means for laterally translating the actuator 60 and the sample holder 50 in a down position 50D (See FIGS. 2B and 3B) in which samples can be readily removed from, or installed on the sample holder 50. The means for lateral translation can include rollers, casters, or slides 68 which can be guided in a track on a support plate having a stop bracket 69 to provide accurate positioning of the sample holder 50 in the up position 50U with respect to the light diffusing assembly 30.

An input line 82 provides electrical input to a power supply 80 via a switch 84, and an output line 86 provides electrical power to the microwave generator 70 for producing microwaves which are guided by the waveguide 72 towards the sulfur bulb 22 to provide light emission therefrom as light rays 26.

FIG. 2A is an enlarged section view taken along the section line 2—2 of FIG. 1, and showing the sample holder in an up position 50U for exposing a light sensitive sample 90a to diffuse light 27 which exits the cavity 33 through an arcuate diffusive portion 36 extending throughout a wall of the light pipe 32. As depicted for illustrative purposes only, the arcuate reflective portion 36 can be equal portions of the light pipe 32. The planar reflector 44 at the end surface 40 (See FIG. 1) is indicated.

The light pipe 32 can be constructed from a light transmissive plastic tube since the sulfur bulb light source 20 produces light efficiently and without significant heat generation. As indicated above, the arcuate diffusive portion 36 can be provided by fastening a diffusive member (not shown) to an inside surface of the light pipe 32. In such construction of the diffusive portion, the portion of the wall of the light pipe 32 in contact with the diffusive member can be a transparent wall.

FIG. 2B indicates schematically how the sample holder 50 is lowered and laterally translated to a down position 50D for removal and/or loading of samples. First, the vertical motion actuation 66D proceeds by actuating the motion actuator 60 to retract the piston rod 62 to achieve the down position 50D of the sample holder 50. Then the horizontal motion 68D is actuated (if that motion is automated), or alternatively, the motion actuator 60 and the sample holder 50 are manually translated via the rollers, casters, or slides 68 into the horizontal position 68D.

Figure 3A:
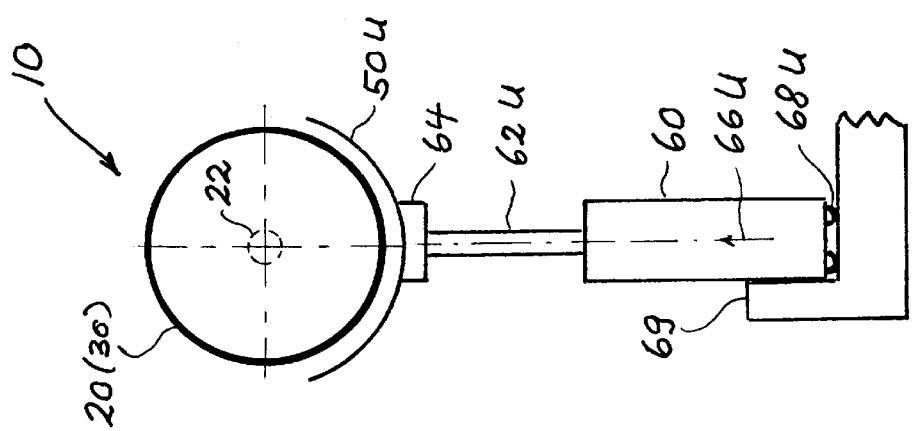
FIG. 3A is a schematic front view of the apparatus of FIG. 1 (with the waveguide removed) showing the sample holder in an up position.
Figure 3B:
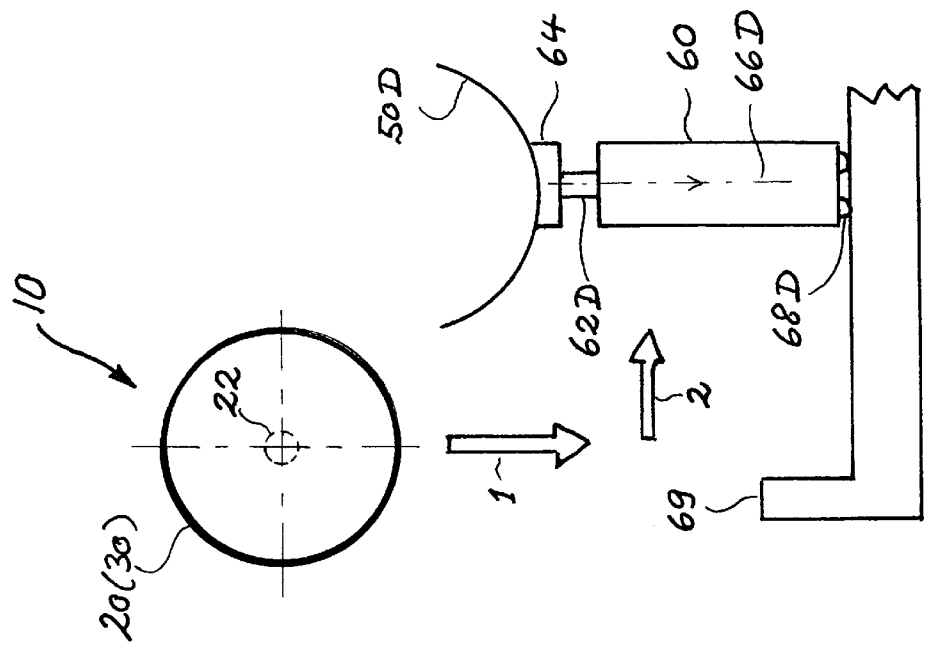
FIG. 3B is a schematic front view of the apparatus of FIG. 1 (with the waveguide removed) and showing the sample holder in a down position.

FIGS. 3A and 3B are schematic front views of the fading apparatus 10, shown with the waveguide 72 (See FIG. 1) removed. FIG. 3A depicts the sample holder 50 in the up position 50U, with the motion actuator 60 resting against a stop bracket 69 to provide accurate positioning of the sample holder 50 with respect to the light diffusing assembly 30. FIG. 3B shows the sample holder 50 in the down position 50D which is achieved by a vertical motion 1, followed by a horizontal motion 2. Upon installing samples for testing, the motion actuator 60 (and the sample holder 50) is first translated laterally (horizontally) to the stop bracket 69, followed by vertical motion actuation 66U to achieve an up position 50U of the sample holder 50.

Figure 4:
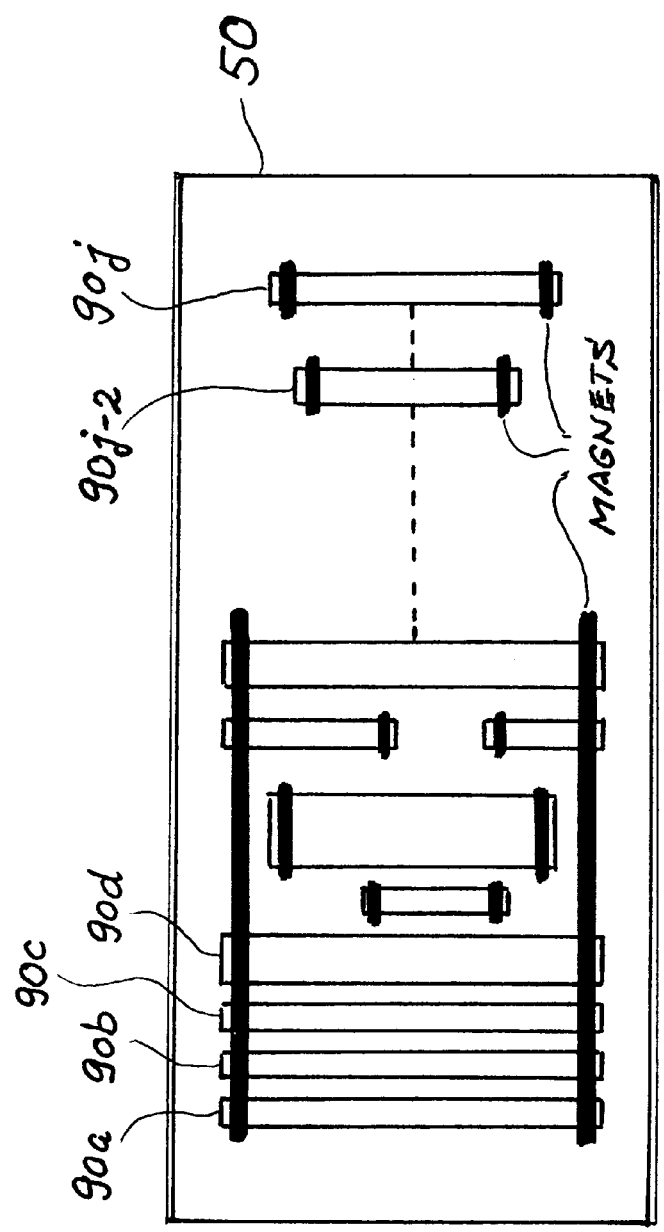
FIG. 4 is a top view of the sample holder shown in FIG. 1 and holding a plurality of samples to be tested.

FIG. 4 is a schematic top view of the sample holder 50. Numerous samples 90a–90j are mounted on the concave side of the arcuate sample holder 50. The sample holder 50 is preferably constructed of a ferromagnetic material such as, for example, steel, vidrel or of alloys, such that the samples can be held in a position of contact with the arcuate surface of the sample holder 50 by magnets or by magnetic strips. This sample holder surface can be coated with a white, diffusely reflective layer (not shown).

The motion actuator 60 can be actuated to provide a vertical motion actuation 66 (U; D) by well-known pneumatic, hydraulic or electromagnetic (solenoid) means. The horizontal motion actuation, if automated, can employ the above means, or a motor-driven spindle transport means.

The sulfur bulb light source 20 is available commercially from Fusion Lighting of Rockville, Md. under the designation or model Solar 1000. Under application of microwave energy to the sulfur bulb 22, the light produced by the bulb 22 has a spectral distribution approximating daylight minus the infrared and ultraviolet components of daylight.

The invention has been described in detail with particular reference to certain preferred embodiments thereof, but it will be understood that variations and modifications can be effected within the spirit and scope of the invention.

PARTS LIST

1 vertical motion of sample holder
2 horizontal motion of sample holder
10 fading apparatus
20 sulfur bulb light source
23 parabolic surface
24 parabolic reflector
26 light rays
27 diffuse light
28 transparent window
30 light diffusing assembly
32 light pipe
33 cavity (of light pipe)
34 arcuate reflective portion
36 acruate diffusive portion
40 end surface
44 planar reflector
50 sample holder
50(U;D) sample holder (Up or Down position)
60 motion actuator (for sample holder)
62 piston rod (Up or Down position)
64 mounting bracket
66(U;D) vertical motion actuation (Up or Down position)
68(U;D) horizontal motion actuators (preceding Up position, and following Down position)
69 stop bracket
70 microwave generator
72 waveguide
74 guided microwaves
80 power supply
82 input line
84 switch
86 output line
90 light sensitive samples (a–j)
CL center line

What is claimed is:

1. Apparatus for subjecting light sensitive materials to visible radiation while minimizing the amount of heat generated to accelerate fading of light sensitive materials, comprising:

(a) a light pipe having a reflective cylindrical surface portion and a light diffusing cylindrical portion defining a cylindrical cavity, the light pipe having first and second end portions disposed on opposite ends of the cylindrical cavity;

(b) a source of visible radiation including at least one microwave energy responsive sulfur bulb disposed adjacent to the first end portion of the cylindrical cavity for directing visible light into the cylindrical cavity;

(c) a reflector disposed in the second end portion of the cylindrical cavity for reflecting light back into such cylindrical cavity; and (d) a holder defining a arcuate surface for receiving flexible light sensitive material disposed adjacent to the light diffusing cylindrical portion of the cylindrical cavity; whereby visible light directed into the cylindrical cavity passes out through the light diffusing cylindrical portion of the cylindrical cavity to illuminate light sensitive material disposed on the arcuate surface of the holder.

2. The apparatus of claim 1 further including means for moving the holder relative to the light pipe.

* * * * *